United States Patent [19]

Webb

[11] Patent Number: 4,710,512

[45] Date of Patent: Dec. 1, 1987

[54] PESTICIDAL COMPOSITIONS EMPLOYING STABILIZED AMITRAZ

[75] Inventor: Michael A. Webb, Bar Hill, England

[73] Assignee: Schering Agrochemicals Limited, England

[21] Appl. No.: 918,342

[22] Filed: Oct. 14, 1986

[30] Foreign Application Priority Data

Oct. 16, 1985 [GB] United Kingdom ................ 8525447

[51] Int. Cl.$^4$ ..................... A01N 37/52; A01N 43/02; A01N 43/22
[52] U.S. Cl. .................................... 514/431; 514/637; 514/970
[58] Field of Search ........................ 514/637, 970, 431

[56] References Cited

U.S. PATENT DOCUMENTS 4,438,137  3/1984  Allan ................................... 544/970
4,479,968 10/1984  Hyman et al. ...................... 514/531

OTHER PUBLICATIONS

Kato et al., C.A. vol. 88 (1978) 88:7978a.
The Merck Index, 10th Ed. (1983) #3535.

Primary Examiner—Allen J. Robinson
Attorney, Agent, or Firm—Ostrolenk, Faber, Gerb & Soffen

[57] ABSTRACT

Liquid formulations of the pesticide amitraz are stabilized by the addition of one or more aluminum alkoxides.

10 Claims, No Drawings

PESTICIDAL COMPOSITIONS EMPLOYING STABILIZED AMITRAZ

This invention relates to pesticidal compositions comprising amitraz.

Amitraz is the common name for the insecticide and acaricide whose chemical name is N-methylbis(2,4-xylyliminomethyl)amine. This compound is commonly formulated as an emulsifiable concentrate, but in this form can suffer from degradation, particularly in hot and/or humid conditions. It is therefore frequently necessary to add a stabilizer. A particularly valuable stabilizer has been epichlorhydrin, but the use of this stabilizer has been banned in some countries. In GB Pat. No. 2058570 is claimed the use of certain carbodiimides, and especially di-(2,6-diisopropylphenyl)carbodiimide as a stabilizer, but these compounds suffer from certain disadvantages. In particular their use has not been cleared, up till now, by certain regulatory authorities but also they do not satisfactorily stabilize formulations to which endosulphan has been added.

We have now found that aluminum alkoxides can act as very good stabilizers for amitraz.

The composition usually comprises from 0.5 to 50%, e.g. 5 to 30% and especially 10 to 20% weight by volume of amitraz, from 0.1 to 5%, e.g. 0.5 to 2% aluminum alkoxide and optionally up to 35% surfactant, preferably from 5 to 25%. As previously stated the aluminum alkoxides are particularly valuable when endosulphan is also present, e.g. in amounts of from 10 to 40%, especially 20 to 30% weight by volume.

Suitable solvents include for example, aromatic hydrocarbons such as alkylbenzenes incorporating the various trimethylbenzenes, methylethylbenzenes, dimethylethylbenzenes, diethylbenzenes, tetramethylbenzenes, trimethylethylbenzenes, methyldiethylbenzenes, pentamethylbenzenes, naphthalene and various methylnaphthalenes and mixtures thereof; chlorinated hydrocarbons such as chlorinated alkanes, chlorinated alkenes and chlorinated benzene and chlorinated alkylbenzenes; ketonic solvents such as cyclohexanone, isophorone, N-methyl-pyrrolidone, disobutylketone and methylisobutylketone.

Surfactants may be any of those commonly used in the art and are preferably nonionic surfactants, anionic surfactants or a blend of nonionic and anionic surfactants.

Nonionic surfactants include for example, ethoxylated alkylphenols such as optionally terminally blocked alkylphenol ethoxylates; ethoxylated aliphatic alcohols; ethoxylated amines; ethoxylated fatty acids and fatty acid esters; ethoxylated alkylolamides; block polymers/copolymers of ethylene oxide and propylene oxide; alkylolamides and ethoxylated/propoxylated alkyl phenols or fatty alcohols.

Anionic compounds include for example, sulphonates such as alkylaryl sulphonates or petroleum sulphonates; sulphonates such as alcohol sulphates or other sulphates; phosphate esters; or sulphosuccinates.

The aluminum alkoxide is generally a $C_{1-6}$ alkoxide. Mixtures of alkoxides may be used and a particularly suitable mixture is that of the isopropoxide and the sec.-butoxide.

Other pesticides may be included in the compositions of the invention, especially endosulphan.

Although the invention is particularly applicable to the stabilization of emulsifiable concentrates, i.e. a concentrate which is diluted with water before use, to form an emulsion of the active ingredient in water, other liquid compositions, containing amitraz may be stabilized according to the invention. For example, a ULV (ultra-low volume) formulation comprising a solution of amitraz and the aluminum alkoxide(s) in a suitable solvent may be prepared for direct spraying without dilution or a pour-on formulation may be prepared for the direct application to animals by dissolving amitraz and the alkoxide in an oil medium which may optionally contain a co-solvent.

The invention is illustrated in the following Examples.

EXAMPLE 1

An emulsifiable concentrate was formulated as follows:

|  | % w/v |
| --- | --- |
| amitraz | 15 |
| endosulphan | 28 |
| Triton CF 10[1] | 13 |
| Aerosol OT-S[2] | 10 |
| Aliso B[3] | 1 |
| Solvesso 200[4] | to 100 |

[1] Benzyl blocked octylphenol ethoxylate
[2] Dioctyl sodium sulphosuccinate (70% in hydrocarbon solvent)
[3] 50:50 mixture of aluminium isopropoxide and sec.-butoxide
[4] Methylnaphthalene fraction For the purpose of comparison, a similar formulation was made up omitting the Aliso B. Samples were stored in 1L tins at temperatures of 40° and 50° C. Water was added to each formulation to ensure an initial water content of 0.1%. After two months, portions of each sample were analysed for decomposition of amitraz, by gas-liquid chromatography.

The results are as follows:

|  | % degradation of amitraz. | |
| --- | --- | --- |
| Temperature | Formulation of Invention | Comparison |
| 40° C. | 0 | 10 |
| 50° C. | 0 | 12 |

It will be seen that the aluminum alkoxides significantly reduced the decomposition of the amitraz.

EXAMPLE 2

An emulsifiable concentrate was formulated as follows:

|  | % w/v |
| --- | --- |
| amitraz | 12.5 |
| Ethylan KEO[5] | 20 |
| Aliso B | 1 |
| Solvesso 200 | to 100 |

[5] Nonyl phenol ethoxylate

This was tested in a similar manner to that described in Example 1 (except that extra water was not added) and compared with a formulation omitting the Aliso B.

The results after three month's storage were are as follows:

| Temperature | % degradation of amitraz. | |
|---|---|---|
| (°C.) | Formulation of Invention | Comparison |
| 20 | 0 | 3 |
| 40 | 0 | 6 |
| 50 | 1 | 8 |

It will be seen that the aluminum alkoxides again significantly reduced the decomposition of the amitraz.

I claim:

1. A liquid pesticide composition which comprises a solution of 0.5 to 50% weight by volume amitraz in an organic solvent, together with a stabilizing amount from 0.1 to 5% weight by volume of at least one aluminum $C_{1-6}$ alkoxide.

2. A composition according to claim 1, wherein the aluminum alkoxide comprises a mixture of aluminum isopropoxide and aluminum sec.-butoxide.

3. A composition according to claim 1 which comprises from 5 to 30% weight by volume of amitraz.

4. A composition according to claim 3 which comprises from 10 to 20% weight by volume of amitraz.

5. A composition according to claim 1 which comprises from 0.5 to 2% weight by volume of aluminum alkoxide.

6. A composition according to claim 1 which additionally comprises from 10 to 40% weight by volume of endosulphan.

7. A composition according to claim 3 which comprises from 0.5 to 2% weight by volume of aluminum alkoxide.

8. A composition according to claim 7 which comprises from 10 to 20% weight by volume of amitraz.

9. A composition according to claim 8 which additionally comprises from 10 to 40% weight by volume of endosulphan.

10. A composition according to claim 9, wherein the aluminum alkoxide comprises a mixture of aluminum isopropoxide and aluminum sec.-butoxide.

* * * * *